United States Patent [19]

Lake et al.

[11] 4,420,639

[45] Dec. 13, 1983

[54] AROMATIC COMPOUNDS

[75] Inventors: Anthony W. Lake, Guildford Surrey; Carl J. Rose, London, both of England

[73] Assignee: Beecham Group Limited, England

[21] Appl. No.: 320,190

[22] Filed: Nov. 12, 1981

Related U.S. Application Data

[60] Continuation of Ser. No. 955,197, Oct. 27, 1978, abandoned, which is a continuation of Ser. No. 795,119, May 9, 1977, which is a division of Ser. No. 748,676, Dec. 8, 1976, Pat. No. 4,061,799, which is a continuation-in-part of Ser. No. 563,159, Mar. 28, 1975, abandoned, which is a division of Ser. No. 501,733, Aug. 29, 1974, abandoned.

[30] Foreign Application Priority Data

Sep. 11, 1973 [GB] United Kingdom ............... 42550/73

[51] Int. Cl.$^3$ ............................................ C07C 49/215
[52] U.S. Cl. ...................................................... 568/328
[58] Field of Search ........................................ 568/328

[56] References Cited

PUBLICATIONS

Chatterjea et al., Indian J. Chem., vol. 11, pp. 214–218 (1973).

*Primary Examiner*—James H. Reamer
*Attorney, Agent, or Firm*—Jacobs & Jacobs

[57] ABSTRACT 4-(6'-Methoxy-2'-naphthyl) butan-2-one is described as having anti-inflammatory activity and an improved therapeutic ratio.

4 Claims, No Drawings

AROMATIC COMPOUNDS

CROSS-REFERENCE

This is a continuation of Ser. No. 955,197 filed Oct. 27, 1978 now abandoned, which is a continuation of Ser. No. 795,119, filed May 9, 1977, which is a divisional of Ser. No. 748,676 filed Dec. 8, 1976, now U.S. Pat. No. 4,061,799, which is a continuation-in-part of Ser. No. 563,159 filed Mar. 28, 1975, now abandoned, which is a divisional of Ser. No. 501,733 filed Aug. 29, 1974, now abandoned.

The present invention relates to pharmaceutically active naphthalene derivatives, to processes for their preparation and to pharmaceutical compositions containing them.

Certain naphthalene derivatives are known to possess useful anti-inflammatory activity and to be suitable for use in the treatment of various rheumatic and arthritic conditions. One particuarly effective naphthalene derivative that has found clinical use is Naproxen which is of the formula (I):

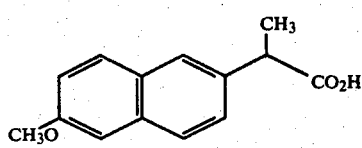

This compound and certain related compounds have been described in British Patent Specifications Nos. 1,271,132; 1,274,271; 1,274,273; 1,291,386; 1,211,134; 1,297,306; 1,276,261; 1,216,882; 1,289,041; 1,321,347 and 1,296,493; in U.S. Pat. Nos. 3,562,336; 3,663,584; 3,626,012; 3,683,015 and 3,651,106; in the Published Specifications of Netherlands Patent Applications Nos. 71/15159 and 71/12833 and in the Published Specifications of German Patent Applications Nos. 2,007,177 and 2,014,030. The pharmacological activities of such compounds have also been described in J. Med. Chem., 13, 203 (1970) and J. Pham. Exp. Thera., 179, 114 (1971)

Unfortunately, the compound of formula (I) can cause severe irritation of the gastro-intestinal tract in some subjects at doses not greatly in excess of the therapeutic dose.

We have found that compounds such as those of the formula

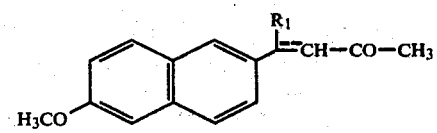

wherein $R_1$ is H or $CH_3$ and the dotted line represents a double bond optionally present do not excessively irritate the stomach at the therapeutic dose. As we have also found that branching at the α-carbon atom tends to impart a degree of oestrogenicity to these compounds, we believe it is advantageous to use a compound unbranched at the α-carbon atom. Similarly as we have found that the carbon-carbon double bond tends to impart a degree of oestrogenicity to these compounds, we believe it is advantageous to use a compound which does not contain this feature.

It is an object of this invention to provide medicaments which possess useful anti-inflammatory activity suitable for the treatment of rheumatic or arthritic conditions while not possessing a high propensity to produce side effects such as gastro-intestinal irritancy or oestrogenic effects. We have found that 4-(6'-methoxy-2'-naphthyl)butan-2-one which is the compound of the formula

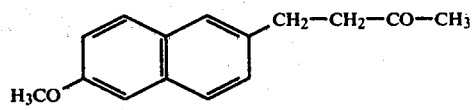

has a good spectrum of anti-inflammatory activity while not causing either oestrogenic effects or pronounced gastric-irritant effects at the therapeutic dose.

J. N. Chatterjea and R. Prasad (Indian J. Chem., 1973 214–8) reported the preparation of a compound which they thought to be 4-(6'-methoxy-2'-naphthyl)butan-2-one. However the compound they reported was an oil whereas we have found that 4-(6'-methoxy-2'-naphthyl)butan-2-one is a solid when pharmaceutically pure. We have also found that crystalline 4-(6'-methoxy-2'-naphthyl)butan-2-one may be prepared. The present invention provides compounds of the formula (II):

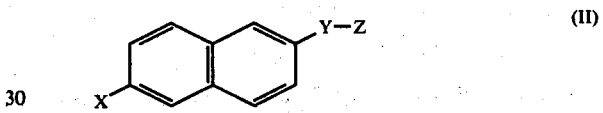

wherein X is a chlorine or bromine atom or a methoxyl, methylthio or alkyl group of 1–4 carbon atoms; Y is a $-CHR_1-CH(R_2)-$, $-CHR_1-CO-$, $-CHR_1-C(OH)R_2-$ or $-C(R_1)=C(R_2)-$ group where $R_1$ and $R_2$ are each a hydrogen atom or a methyl, ethyl group or propyl group and Z is a $R_4$, $(CH_2)_nCOR_4$, $(CH_2)_nCH(OH)R_4$ or $(CH_2)_nC(CH_3)(OH)R_4$ group where $R_4$ is an alkyl group of 1 to 4 carbon atoms and n is 0, 1 or 2; with the proviso that Y-Z contains at least one oxygen atom and not more than one carbonyl group.

Most suitably X is methoxyl or methylthio.

One especially suitable sub-group of compounds of formula (II) are those of formula (III):

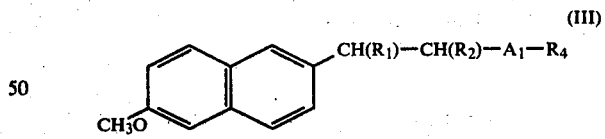

wherein $R_1$, $R_2$ and $R_4$ are defined in relation to formula (II) and $A_1$ is a CO or CHOH group.

In compounds of formula (III) $R_1$ is preferably a hydrogen atom or methyl group, $R_2$ is preferably a hydrogen atom and $R_4$ is preferably a methyl or propyl group. Most suitably suitably $A_1$ is a CO group. Such compounds include, for example, those wherein the side chain is a group selected from —$CH_2$—$CH_2$—CO—$CH_3$
—$CH(CH_3)$—$CH_2$—CO—$CH_3$
—$CH(CH_3)$—$CH_2$—CO—$CH_2$—$CH_2$—$CH_3$
or
—$CH_2$—$CH_2$—CHOH—$CH_3$ The compounds of formula (III) wherein $R_1$ is a hydrogen atom or methyl group, $R_2$ is a hydrogen atom, $A_1$ is CO and $R_4$ is a methyl group are particularly suitable.

A further especially suitable sub-group of compounds of formula (II) are those of formula (IV):

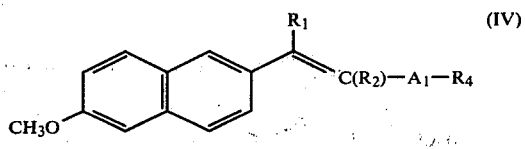

wherein $R_1$, $R_2$, $R_4$ and $A_1$ are as defined in relation to formula (III).

In compounds of formula (IV), $R_1$ is preferably a hydrogen atom or methyl group, $R_2$ is preferably a hydrogen atom and $R_4$ is preferably a methyl group. Most suitably $A_1$ is a CO group.

In a further aspect, the present invention provides a process for the preparation of compounds of the formula (V):

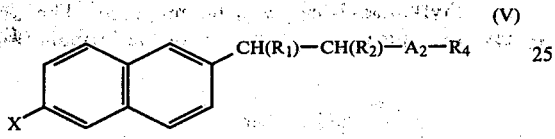

wherein X, $R_1$, $R_2$ and $R_4$ are as defined in relation to formula (II) and $A_2$ is a CO, CHOH or $C(CH_3)OH$ group, which process comprises the reaction of a compound of the formula (VI):

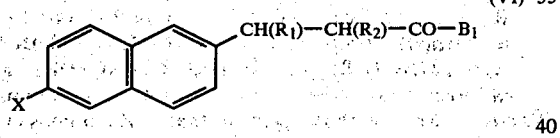

where $B_1$ is a chlorine or bromine atom; with a compound of the formula (VII):

where $R_4B_2$ is an alkyl metal derivative to yield a compound of the formula (VIII):

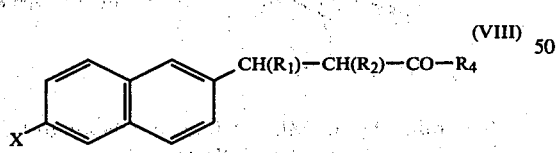

and thereafter optionally reducing the compound (VIII) in conventional manner to yield a compound of the formula (V) wherein $A_2$ is a CHOH group or else optionally reacting the compound of the formula (VIII) with a conventional methyl metal compound to produce a compound of the formula (V) wherein $A_2$ is a $C(CH_3)OH$ group.

The conventional and preferred compound (VII) is an alkyl lithium compound.

As is common in chain extension reactions using metal derivatives, the reaction is carried out in an inert, aprotic solvent at a depressed temperature and preferably under an inert atmosphere. For example, the reaction may be carried out at below $-40°$ C. in dry diethylether.

Normally, an additive such as cuprous iodide is present during the reaction.

It will be realized that compounds of the formula (V) wherein $A_2$ is a CO group are valuable materials which (quite independently of the method of their production) can serve as intermediates in the production of the compounds of formula (V) wherein $A_2$ is a CHOH or $C(CH_3)OH$ group.

The reduction of compounds of formula (V) wherein $A_2$ is a carbonyl group to the corresponding secondary alcohol may take place using conventional methods of reduction such as hydrogenation in the presence of a transition metal catalyst or by the use of a hydride such as $NaBH_4$, $LiAlH_4$ or the like.

Similarly, the production of the tertiary alcohols of formula (V) from the corresponding ketones may utilize conventional methods such as reaction with a $CH_3MgCl$, $CH_3MgBr$, $CH_3MgI$, $CH_3Li$ or the like.

In another aspect of the process of this invention, it provides a process for the preparation of compounds of the formula (IX):

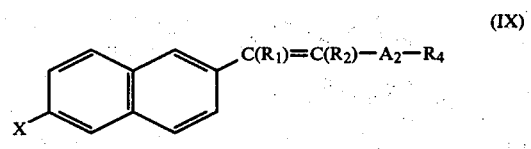

wherein X, $R_1$, $R_2$ and $R_4$ are as defined in relation to formula (II) and $A_2$ is a CO, CHOH or $C(CH_3)OH$ group which process comprises the reaction of a compound of the formula (X):

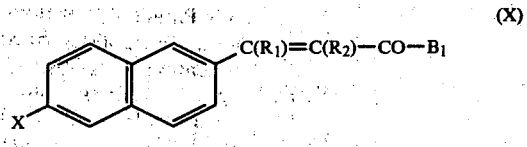

where $B_1$ is a chlorine or bromine atom; with a compound of the formula (VII) as previously defined to yield a compound of the formula (XI):

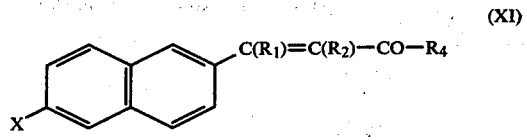

and thereafter optionally reducing the compound of formula (XI) in a manner which converts the CO group a CHOH group or optionally reacting the compound of formula (XI) with a conventional methyl metal compound to produce a compound of the formula (IX) wherein $A_2$ is a $C(CH_3)OH$ group: [the later reaction is sometimes complicated by 1-4 addition reactions which can reduce yields of the compound of the formula (XI)].

The conventional and preferred compound of formula (VII) is an lakyl lithium compound.

The chain extension reaction may take place under the general conditions outlined above.

It will be realised that compounds of the formula (IX) wherein $A_2$ is a CO group are valuable materials which (quite independent of the method of their production) can serve as intermediates in the production of compounds of formula (IX) wherein $A_2$ is a CHOH or $C(CH_3)OH$ group.

In another aspect, the present invention provides a process for the preparation of a compound of the formula (XII):

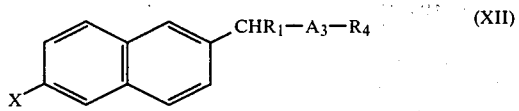

wherein X, $R_1$ and $R_4$ are as defined in relation to formula (II) and $A_3$ is a CO or $C(OH)R_2$ where $R_2$ is as defined in relation to formula (II) which process comprises the reaction of a compound of the formula (XIII):

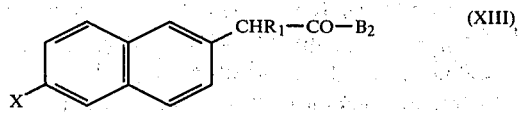

where $B_1$ is a chlorine or bromine atom; with a compound of the formula (VII) as previously defined to yield a compound of the formula (XIV):

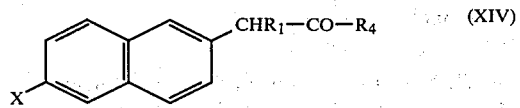

and thereafter optionally reducing the compound (XIV) in conventional manner to yield a compound of the formula (XII) wherein $A_3$ is a CHOH group or else optionally reacting the compound of formula (XIV) with a conventional methyl metal or ethyl metal compound to produce a compound of formula (XII) wherein $A_3$ is a $C(OH)CH_3$ or $C(OH)C_2H_5$ group.

The compound of formula (VII) is conventionally and preferably an alkyl lithium compound.

The chain extention, reduction and addition reactions may be carried out under the previously described general conditions.

In a further aspect, this invention provides a process for the preparation of compounds of the formula (XV):

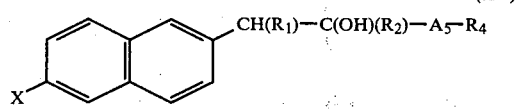

wherein X, $R_1$, $R_2$, and $R_4$ as defined in relation to formula (II) and $A_5$ is a CO, CHOH or $C(CH_3)OH$ group which process comprises the hydration of a compound of the formula (XVI):

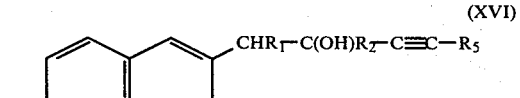

wherein $R_5$ is a hydrogen atom or an alkyl group of 2 to 3 carbon atoms in the presence of a mercuric salt to yield a compound of the formula (XVII):

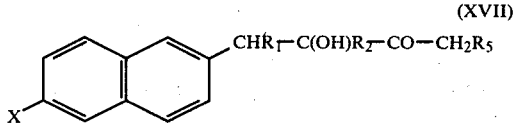

and thereafter if desired, reducing the carbonyl group to a CHOH group in conventional manner or else reacting the carbonyl group with an alkyl metal compound to form a terminal $C(OH)(CH_3)R_4$ group in conventional manner.

The preparation of compounds of formula (XV) wherein $A_5$ is a CHOH or $C(CH_3)OH$ group by the reduction or alkylation of the corresponding compound wherein $A_5$ is a CO group, forms an aspect of this invention irrespective of the method of production of the keto compound.

The compound of formula (XVI) may be prepared by the reaction of a compound of the formula (XVIII):

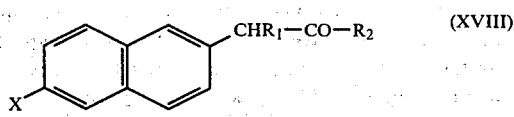

where X, $R_1$ and $R_2$ as defined in relation to formula (II) with an acetylide ion of the formula $\ominus C\equiv C.R_5$ which has been generated in conventional manner.

Compounds of the formula (II) wherein X is a methoxyl group may be prepared by methylation under conventional reaction conditions of the corresponding compound of formula (II) wherein X is a hydroxyl group or an anion thereof.

Compounds of the formula (II) wherein XY is a $CH=CH-CO-CH_3$ group may be prepared from a compound of the formula (XVIX):

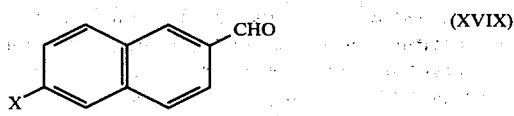

by base catalysed condensation with acetone.

Compounds of the formula (II) wherein XY is a $CHR_1-CH_2-CO-R_4$ group may be prepared by the reduction of a compound of the formula (XV):

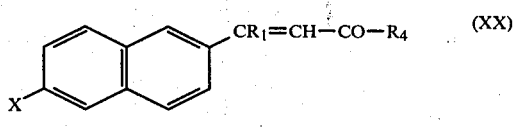

Such reduction reactions may be effected by hydrogenation using a conventional transition metal catalyst such as palladium on charcoal. Such reactions are normally carried out in an innert organic solvent at ambient temperature using an atmospheric or slightly superatmospheric pressure of hydrogen.

Compounds of the formula (II) wherein XY is a $CHR_1.CH.CO.CH_3$ may be prepared by the reaction of a compound of the formula (XXI):

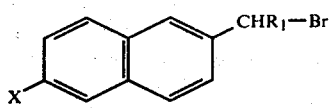

with acetylacetone in the presence of a base. Such reactions are generally carried out in an organic solvent such as a lower alkanol at an elevated temperature, for example, in ethanolic solution under reflux. Suitable bases are those which promote formation of the anion of acetylacetone without causing expulsion of the bromine atom. A suitable base is potassium carbonate. For such a reaction $R_1$ is preferably hydrogen.

Compounds of formula (II) often include assymetric centres and therefore, exist in various optical forms. All such forms are included within this invention.

Compounds of formula (II) have anti-inflammatory and/or analgeasic activity. Accordingly, pharmaceutical compositions are included within the scope of this invention which compositions comprise a compound of formula (II) together with a pharmaceutically acceptable carrier.

The compositions of this invention may be in any conventional form but in general, orally administrable unit dosage compositions such as tablets or capsules are preferred. Such dosage forms will normally contain from 20 mg to 1000 mg and more usually from about 100 mg to 600 mg. Such dosage forms may be taken one or more times a day (preferably 2 to 4 times a day) so that the daily dose is normally between 300 mg and 3000 mg and more usually from 500 mg to 2000 mg, for example 600 mg to 1600 mg.

EXAMPLE 1

Ethyl 3-(6'-methoxy-2'-naphthyl)-2-butenoate

Sodium hydride (10.8 g., 60% dispersion in mineral oil) was washed three times with cyclohexane and blown dry in a stream of nitrogen. Dry 1,2-dimethoxyethane (150 ml) was added and the slurry was stirred at room temperature. Triethyl phosphonoacetate (54 g.) was added dropwise and the mixture stirred at room temperature for 1 hour under nitrogen. A solution of 2-acetyl-6-methoxynaphthalene (30 g.) in 1,2-dimethoxyethane (300 ml) was run in and the solution refluxed overnight under nitrogen.

The reaction mixture was diluted with water, acidified and extracted with ether. The ethereal layer was washed with sodium carbonate solution and with water, dried over anhydrous magnesium sulphate and evaporated to give ethyl 3-(6'-methoxy-2'-naphthyl)-2-butenoate as a yellow solid in quantitative yield. The product was shown by NMR to be predominantly the trans isomer.

NMR: Trans vinylic proton 3.69τ, cis vinylic proton 4.0τ. —CO$_2$CH$_2$CH$_3$: triplet (3 protons) at 8.62τ, J=11.5 cps. quarter (2 protons) or 5.71τ, J=11.5 cps. —CH$_3$: two peaks very close together at —7.28τ, equivalent to 3 protons in total.

IR; Carbonyl absorption at 1708 cm$^{-1}$.

EXAMPLE 2

Ethyl 3-(6'-methoxy-2'-naphthyl)-butyrate

Ethyl 3-(6'-methoxy-2'-naphthyl)-2-butenoate (24 g.) was taken up in ethyl acetate (100 ml) and 10% Pd/C (2.4 g.) added. The mixture was hydrogenated at room temperature and 50 psi pressure for two hours.

The catalyst was removed by filtration and the filtrate evaporated to give ethyl 3-(6'-methoxy-2'-naphthyl)-butyrate as a colourless solid in quantitative yield.

IR: Saturated ester carbonyl absorption at 1730 cm$^{-1}$.
NMR:

3 proton doublet at 8.68τ, J=11 cps.
Absence of vinylic protons.

EXAMPLE 3

3-(6'-Methoxy-2'-naphthyl)-butyric acid

Ethyl 3-(6'-methoxy-2'-naphthyl)-butyrate (14.4 g.) was taken up in methanol (300 ml) and 10% sodium hydroxide solution (150 ml) and the mixture was refluxed for 2 hours. The reaction mixture was diluted with water and extracted with ethyl acetate. The aqueous layer was acidified and extracted with ethyl acetate. The acid extract was washed with water, dried over anhydrous magnesium sulphate and evaporated to give 3-(6'-methoxy-2'-naphthyl)-butyric acid as a white solid (11.9 g., 92%), mp. 126°-129°.

IR: carbonyl absorption at 1700 cm$^{-1}$.

EXAMPLE 4

4-(6'-methoxy-2'-naphthyl)-pentan-2-one

Thionyl chloride (8.15 ml) was added dropwise to a solution of 3-(6'-methoxy-2'-naphthyl)-butyric acid (19.0 g) in dry benzene (200 ml) and the mixture was gently refluxed overnight. The solvent was evaporated to give the crude acid chloride as a brown oil.

Methyl lithium (253 ml., 2.18 M in ether) was diluted to 2 liters with dry ether, cooled to 0° C. and stirred under nitrogen. Cuprous iodide (48.6 g) was added and stirring continued for 10 minutes. The mixture was cooled to −70° C. and a solution of the crude acid chloride in ether (250 ml) was run in. The mixture was stirred under nitrogen at −70° C. for 15 minutes. Methanol (350 ml) was added to quench the reaction and the mixture was diluted with water and acidified. Kieselguhr was added to aid filtration and the reaction mixture was filtered through a pad of Kieselguhr. The ether layer was washed with sodium carbonate solution and with water, dried over anhydrous magnesium sulphate and evaporated to give a brown oil. The product was purified by short column chromatography to give 4-(6'-methoxy-2'-naphthyl)-pentan-2-one as a pale yellow oil, which solidified slowly on standing. Yield 10.7 g., 57τ.

IR: Carbonyl absorption at 1705 cm$^{-1}$.
NMR: CH$_3$CO—:3 proton singlet at 8.01τ

3 proton doublet at 8.72τ, J=11 cps.

EXAMPLE 5

2-Acetyl-6-methoxynapthalene

Powdered anhydrous aluminium chloride (100 g) was taken up in dry nitrobenzene (600 ml) and the mixture stirred in an ice-bath. 2-methoxynaphthalene (96 g) was added and acetyl chloride (54.5 ml) was run in dropwise over a period of 15 minutes. The ice-bath was removed after 3 hours and the mixture was stirred for a further 3 days.

The reaction mixture was poured into a solution of crushed ice, concentrated hydrochloric acid (200 ml) and water (200 ml) and extracted with ether. The ethereal layer was washed with water till neutral, dried over anhydrous magnesium sulphate and evaporated. The residual nitrobenzene was removed by vacuum distillation and the dark-brown residue which remained was fractionally distilled to give 2-acetyl-6-methoxynaphthalene as a yellow solid b.p. 155°-160°/0.4 mm Hg as the major fraction. This was melted and poured into methanol (300 ml). The colourless crystals (24.6 g mp. 109°-110°) which separated were collected by filtration, washed with methanol and dried in a vacuum desiccator. Further amounts of product could be obtained by concentration of the mother liquors.

EXAMPLE 6

2-(6'-methoxy-2'-naphthyl)-acetic acid

A mixture of 2-acetyl-6-methoxynaphthalene (213 g), sulphur (38.4 g) and morpholine (120 ml) was refluxed overnight. The crude thiomorpholide intermediate was purified by trituration with ether, taken up in ethanol (300 ml) and 10% potassium hydroxide solution (1000 ml) and refluxed for 4 hours.

The product mixture was filtered and extracted with ethyl acetate. The aqueous layer was acidified and the precipitate filtered, washed with water and dried to give 2-(6'-methoxy-2'-naphthyl)-acetic acid as a cream solid (107.2 g, 46.6%), mp. 158°-162°.

NMR: 2 proton singlet (—CH$_2$—) at 6.23$\tau$.

EXAMPLE 27

Methyl 2-(6'-methoxy-2'-naphthyl)-acetate 2-(6'-methoxy-2'-naphthyl)-acetic acid (26.89 g) was taken up in methanol (120 ml) and acetyl chloride (15.5 ml) and gently refluxed for 2 hours. The reaction mixture was diluted with water and extracted with ether. The ethereal layer was washed with sodium carbonate solution and with water, dried over anhydrous magnesium sulphate and evaporated to give methyl 2-(6'-methoxy-2'-naphthyl)-acetate as a pink solid (24.9 g, 87%) m.p. 75° NMR: 3 proton singlet (—CO$_2$CH$_3$) at 6.29$\tau$.

EXAMPLE 8

Methyl 2-(6'-methoxy-2'-naphthyl)-butyrate

Sodium (2.5 g) and a few crystals of ferric nitrate were added to liquid ammonia (200 ml distilled from sodium) and the mixture was stirred for 2 hours. Methyl 2-(6'-methoxy-2'-naphthyl)-acetate (24.9 g) in anhydrous tetrahydrofuran (60 ml) was added and stirring continued for 15 minutes. Ethyl iodide (7.9 ml) in tetrahydrofuran (10 ml) was cautiously added and the mixture stirred for 2 hours. Ammonium chloride (7 g) was added and the ammonia was allowed to evaporate overnight.

The reaction mixture was diluted with water and extracted with ether. The ethereal layer was washed with sodium bicarbonate solution, with sodium chloride solution and with water, dried over anhydrous magnesium sulphate and evaporated to give methyl 2-(6'-methoxy-2'-naphthyl)-butyrate as a yellow solid (27.4 g, 98%), m.p. 69°-71° NMR: 3 proton triplet (CH$_3$—CH$_2$—) at 9.09$\tau$, J=12 cps.

The experiment was repeated using sodium (1.05 g), liquid ammonia (200 ml), methyl 2-(6'-methoxy-2'-naphthyl)-acetate (10.5 g) and methyl iodide (2.8 ml). Work-up as above gave methyl 2-(6'-methoxy-2'-naphthyl)-propionate as a yellow solid (10.3 g, 92.5%) NMR: 3 proton doublet ($^1$CH$_3$—CH—) at 8.41$\tau$, J=12 cps.

The experiment was repeated using sodium (1.0 g), liquid ammonia (100 ml), methyl 2-(6'-methoxy-2'-naphthyl)-acetate (10 g) and 1-bromopropane (3.15 ml). Work up as above gave a brown oil, purified by short column chromatography to give methyl 2-(6'-methoxy-2'-naphthyl)-valerate as a yellow solid (6.49 g, 55%).

EXAMPLE 9

2-(6'-methoxy-2'-naphthyl)-butyric acid

Methyl 2-(6'-methoxy-2'-naphthyl)-butyrate (27.4 g) was taken up in methanol (300 ml) and 10% sodium hydroxide solution (150 ml) and refluxed for 2 hours.

The reaction mixture was diluted with water and extracted with ethyl acetate. The aqueous layer was acidified, extracted with ethyl acetate and the organic layer washed with water, dried over anhydrous magnesium sulphate and evaporated to give 2-(6'-methoxy-2'-naphthyl)-butyric acid as an orange solid (25.8 g, 99%), mp. 125°-131°.

The experiment was repeated using methyl 2-(6'-methoxy-2'-naphthyl)-propionate (10.3 g), methanol (200 ml) and 10% sodium hydroxide solution (100 ml). Work up as above gave an orange solid (9.3 g, 96%) which was recrystallised from ether to give 2-(6'-methoxy-2'-naphthyl)propionic acid as a yellow solid mp. 148°-153°.

The experiment was repeated using methyl 2-(6'-methoxy-2'-naphthyl)-valerate (6.49 g), methanol (90 ml) and 10% sodium hydroxide solution (45 ml). Work up as above gave 2-(6'-methoxy-2'-naphthyl)-valeric acid as a cream solid (5.2 g, 84%).

EXAMPLE 10

3-(6'-methoxy-2'-naphthyl)-pentan-2-one 2-(6-methoxy-2'-naphthyl)-butyric acid (23.9 g) was taken up in dry benzene (100 ml) and thionyl chloride (11.5 ml) in benzene (10 ml) was added dropwise. The mixture was gently refluxed overnight. The solvents were removed by evaporation to give the crude acid chloride.

Methyl lithium (311 ml, 2.2 M solution in ether) was diluted to 1800 ml with dry ether, cooled to 0° and stirred under nitrogen. Cuprous iodide (59.5 g) was added and stirring continued for 10 minutes.

The mixture was cooled to −70° and a solution of the acid chloride in dry ether (400 ml) was added. The mixture was stirred at −70° under nitrogen for 15 minutes.

Methanol (250 ml) was added to quench the reaction and the reaction mixture was allowed to come to room temperature, diluted with water and acidified with dilute hydrochloric acid. Kieselguhr was added and the mixture was filtered. The ethereal layer of the filtrate was separated, washed with sodium carbonate solution and with water, dried over anhydrous magnesium sulphate and evaporated to a brown oil, which was purified by short column chromatography to give 3-(6'-methoxy-2'-naphthyl)-pentan-2-one as a pale yellow solid (14.2 g, 60%), mp. 56°–59°. Infra red carbonyl absorption at 1705 cm$^{-1}$.

NMR: 3 proton singlet (CH$_3$CO—) at 7.9τ.

The experiment was repeated using 2-(6'-methoxy-2'-naphthyl)-acetic acid (5.0 g), thionyl chloride (2.4 ml) methyl lithium (60 ml, 1.95 m) and cuprous iodide (12.1 g). Work up as above gave a brown solid (4.7 g, 95%), which was purified by short column chromatography to give 1-(6'-methoxy-2'-naphthyl)-propan-2-one as a yellow solid mp. 69°–72°. NMR: 3 proton singlet (CH$_3$CO—) at 7.8τ.

The experiment was repeated using 2-(6'-methoxy-2'-naphthyl)-propi acid (16.4 g), thionyl chloride (7.2 ml), methyl lithium (180 ml, 1.95 m and cuprous iodide (36.3 g). Work up as above gave a yellow oil (15.9 g, 98%), which was purified by short column chromatography to give 3-(6'-methoxy-2'-naphthyl)-butan-2-one as a yellow solid, mp. 68°–69°. NMR: 3 proton singlet (CH$_3$CO—)at 7.94τ.

The experiment was repeated using 2-(6'-methoxy-2'-naphthyl)-valeric acid (5.2 g), thionyl chloride (2.1 ml), methyl lithium (66.6 ml, 2.18 M) and cuprous iodide (13.1 g). Work up as above gave a yellow oil purified by short column chromatography to give 3-(6'-methoxy-2'-naphthyl)-hexan-2-one as a pale yellow oil (4.5 g, 87%)- NMR: 3 proton singlet (CH$_3$CO—) at 8.0τ.

EXAMPLE 11

3-Hydroxy-3-methyl-4-(6'-methoxy-2'-naphthyl)-1-hexyne

Ethyl magnesium bromide (0.24 mole) was prepared from ethyl bromide (25.5 ml) and magnesium (6.15 g) in dry tetrahydrofuran (150 ml) under nitrogen.

Acetylene was bubbled through dry tetrahydrofuran (100 ml) for 30 minutes. Bubbling was continued while the warm ethyl magnesium bromide solution was added dropwise. Acetylene was bubbled through for a further 45 minutes after addition was complete.

3-(6'-methoxy-2'-naphthyl)-pentan-2-one (9.19 g, 0.038 mole) in dry tetrahydrofuran (50 ml) was added dropwise at room temperature to the stirred Grignard reagent. Stirring was continued overnight.

The reaction mixture was poured into 5% ammonium chloride solution and extracted with ether. The ethereal layer was washed with water, dried over anhydrous magnesium sulphate and evaporated to a brown oil, which was purified by short column chromatography to give 3-hydroxy-3-methyl-4-(6'-methoxy-2'-naphthyl)-1-hexyne as a yellow oil (5.2 g, 51%). Infra-red: absence of carbonyl absorption, —C≡CH absorption at 3300 cm$^{-1}$. (C-H stretching), broad—OH absorption at 3500 cm$^{-1}$.

The experiment was repeated using ethyl magnesium bromide (0.24 mole) and 3-(6'-methoxy-2'-naphthyl)-hexan-2-one (9.8 g). Work up as above gave a brown oil purified by short column chromatography to give 3-hydroxy-3-methyl-4-(6'-methoxy-2'-naphthyl)-1-heptyne as a yellow resin (8.99 g, 83%). Infra-red: absence of carbenyl absorption, —C≡CH absorption at 3300 cm$^{-1}$, —OH absorption at 3500 cm$^{-1}$.

EXAMPLE 12

3-Hydroxy-3-methyl-4-(6'-methoxy-2'-naphthyl)-hexan-2-one

3-Hydroxy-3-methyl-4-(6'-methoxy-2'-naphthyl)-1-hexyne (5.2 g) was taken up in tetrahydrofuran (60 ml) and dilute sulphuric acid (40 ml) and mercuric sulphate (375 mg) was added. The mixture was gently refluxed for two hours.

The reaction mixture was diluted with water and extracted with ethyl acetate. The organic layer was washed with water, dried over anhydrous magnesium sulphate and evaporated to give 3-hydroxy-3-methyl-4-(6'-methoxy-2'-naphthyl)-hexan-2-one as a yellow oil (5.34 g, 96%). Crystallisation from 60°–80° petrol gave the product as a colourless solid, mp. 94°–97°. Infra-red: carbonyl absorption at 1705 cm$^{-1}$, —OH absorption at 3490 cm$^{-1}$. NMR: 3 proton singlet (CH$_3$CO—) at 7.61τ.

The experiment was repeated using 3-hydroxy-3-methyl-4-(6'-methoxy-2'-naphthyl)-1-pentyne (5 g), tetrahydrofuran (60 ml), dilute sulphuric acid (40 ml) and mercuric sulphate (250 mg). Work-up as above gave a brown oil purified by short column chromtography to give 3-hydroxy-3-methyl-4-(6'-methoxy-2'-naphthyl)-pentan-2-one as a cream solid (2.18 g, 41%), mp 72°–74°. Infra-red carbonyl absorption at 1690 cm$^{-1}$.

The experiment was repeated using 3-hydroxy-3-methyl-4-(6'-methoxy-2'-naphthyl)-1-heptyne (7.5 g), tetrahydrofuran (120 ml), dilute sulphuric acid (80 ml) and mercuric sulphate (750 mg). Work up as above gave a brown oil (7.7 g, 96%), which was purified by short column chromatography to give 3-hydroxy-3-methyl-4-(6'-methoxy-2'-naphthyl)-heptan-2-one as a yellow solid mp. 89°–90°. Infra-red carbonyl absorption at 1700 cm$^{-1}$.

EXAMPLE 13

Trans-3-(6'-methoxy-2'-naphthyl)-2-butenoic acid

Ethyl trans-3(6'-methoxy-2'-naphthyl)-2-butenoate (27.4 g) was taken in methanol (600 ml) and 10% sodium hydroxide solution (300 ml) and the mixture refluxed for 2 hours. The sodium salt of the required acid product crystallised out and was filtered off. The filtrate was extracted with ethyl acetate and the aqueous layer was separated.

The sodium salt of the acid was suspended in the aqueous layer and the mixture was acidified. Ethyl acetate was added and the mixture warmed until all the solid had dissolved. The ethyl acetate layer was separated, washed with water, dried over anhydrous magnesium sulphate and evaporated to give a pale yellow solid (20.7 g). The product was recrystallised from ethyl acetate to give trans-3-(6'-methoxy-2'-naphthyl)-2-butenoic acid as a colourless solid (15.9 g, 67.8%), mp. 195°–204°.

IR (Nujol): Carbonyl absorption at 1680 cm$^{-1}$.

EXAMPLE 14

Trans-4-(6'-methoxy-2'-naphthyl)-pent-3-ene-2-one

Thionyl chloride (8.15 ml) was added dropwise to a solution of trans-3-(6'-methoxy-2'-naphthyl)2-butenoic acid (14.0 g) in dry benzene (140 ml) and the mixture was gently refluxed for 4 hours. The solvent was evaporated to give the crude acid chloride as a brown oil.

Methyl lithium (173.3 ml, 2.1 M in ether) was diluted to 1200 ml. with dry ether, cooled to 0° C. and stirred under nitrogen. Cuprous iodide (34.75 g) was added and stirring continued for 10 minutes. The mixture was cooled to −70° C. and a solution of the crude acid chloride in ether (150 ml) was run in. The mixture was stirred under nitrogen at −70° for 15 minutes. Methanol (150 ml) was added to quench the reaction and the mixture was diluted with water and acidified. Kieselguhr was added to aid filtration and the reaction mixture was filtered through a pad of Kieselguhr. The ether layer was washed with sodium carbonate solution and with water, dried over anhydrous magnesium sulphate and evaporated to give a yellow solid. The product was purified by short column chromatography and recrystallisation from 60–80″ petrol to give trans-4-(6′-methoxy-2′-naphthyl)-pent-3-ene-2-one as a pale yellow solid (11.5 g, 82.8%), mp. 98°–101° C. IR (Nujol): Carbonyl absorption at 1680 cm$^{-1}$ NMR: Vinylic proton singlet at 3.30

$CH_3CO-$: 3 proton singlet at 7.30

EXAMPLE 15

4-(6′-Methoxy-2′-naphthyl)-pentan-2-ol

To a solution of 4-(6′-methoxy-2′-naphthyl)-pentan-2-one (2 g) in methanol (100 ml), cooled in ice, was added sodium borohydride (1 g). The solution was stirred for 1 hour, acidified with dil. HCl and extracted with ether (100 ml×3). The water-washed ether extracts were dried (anh. $Na_2SO_4$) and evaporated, giving a clear colourless oil (1.3 g).

IR 3400 cm$^{-1}$ (OH). No C=O absorption apparent.

EXAMPLE 16

4-(6′-Methoxy-2′-naphthyl)-pentan-2-ol 4-(6′-Methoxy-2′-naphthyl)-pentan-2-one (2 g) in ether (100 ml) was added to a Grignard prepared from methyl iodide (1.0 ml) and magnesium (0.5 g) in ether (100 ml). The mixture was refluxed for 1 hour, cooled and decomposed with saturated ammonium chloride solution. Extraction with ether and evaporation gave a clear colourless oil (1.5 g).

IR 3350 cm−(OH). No C=O absorption apparent.

EXAMPLE 17

4-(6′-Methoxy-2′-naphthyl)butan-2-one formulated as tablets

Tablets containing 100 mg of active ingredient may be prepared as follows:

A powder of the following composition excluding the dried starch may be granulated, the dried starch then added and the resultant mixture compressed to give tablets:

|  | mg/tablet |
| --- | --- |
| 4-(6′-methoxy-2′-naphthyl) butan-2-one | 100 |
| lactose | 306 |
| magnesium stearate | 2 |
| starch | 12 |
| pre-gelatinised starch | 30 |
|  | 450 mg total |

EXAMPLE 18

4-(6′-Methoxy-2′-naphthyl)butan-2-one formulated in capsules

Capsules for oral administration containing (i) 200 mg and (ii) 150 mg of active ingredient may be prepared as follows:

(i) Size 00 hard gelatine capsules may be filled with a blended powder of the following composition:

|  | mg/capsule |
| --- | --- |
| 4-(6′-methoxy-2′-naphthyl) butan-2-one | 200 |
| lactose | 200 |
| magnesium stearate | 2 |
| starch (dried) | 10 |
| pre-gelatinised starch | 38 |
|  | 450 mg total |

(ii) Size 0 hard gelatine capsules may be filled with a blended powder of the following composition:

|  | mg/capsule |
| --- | --- |
| 4-(6′-methoxy-2′-naphthyl) butan-2-one | 150 |
| lactose | 120 |
| magnesium stearate | 2 |
| starch (dried) | 8 |
| pre-gelatinised starch | 20 |
|  | 300 mg total |

EXAMPLE 19

4-(6′-Methoxy-2′-naphthyl)-butan-2-one

Methyl (6′-methoxy-2′-naphthyl)acetate (18.9 g) was added to lithium aluminiumhydride (9.5 g) in dry ether (500 ml). The mixture was refluxed for 5 hours and decomposed (2 N $H_2SO_4$). The ether layer was separated, the aqueous layer was extracted with ether and the two ether extracts combined. The combined extract was washed with water, dried with anhydrous $Na_2SO_4$ and evaporated to yield a 2-(6′-methoxy-2′-naphthyl)ethanol as a white solid (13.7 g) m.p. 115°–6° C. Recrystallisation from benzene did not increase the melting point.

Recrystallised 2-(6′-methoxy-2′-naphthyl)ethanol (1 g), phosphorous tribromide (1 ml) and benzene (25 ml) were refluxed for 4 hours. The mixture was then allowed to cool and poured into water (50 ml) and the benzene layer was separated. The aqueous layer was extracted with benzene (25 ml) and the benzene layers combined, washed well with water, dried with anhydrous sodium sulphate and evaporated to give an oil (1 g) which solidified. Extraction and crystallisation from 80°–100° petroleum ether gave 1-bromo-2-(6′-methoxy-2′-naphthyl)ethane (600 mg) m.p. 60° C.

1-Bromo-2-(6′-methoxy-2′-naphthyl)ethane (4.2 g), potassium cyanide (3.3 g), water (50 ml) and ethanol (90 ml) were refluxed for 4 hours. The resulting solution was diluted with water (100 ml) and extracted with ether (3×100 ml). The combined ether extracts were washed with water and then dried with anhydrous sodium sulphate. Evaporation of the ether yielded an oil (3.8 g) containing two components as indicated by thin layer chromatography. Column chromatography (silica gel support, benzene solvent) gave 2-(6'-methoxy-2'-naphthyl)propionitrile (2 g) m.p. 103° C.

2-(6'-Methoxy-2'-naphthyl)propionitrile (1 g) in ether (100 ml) was added to methyl magnesium iodide [from methyliodide (1.4 g) and magnesium (24 mg)] in ether (100 ml). The mixture was refluxed for 1 hour, allowed to stand overnight and dicomposed with dilute hydrochloric acid (100 ml). The ether layer was separated, washed with water and dried with anhydrous sodium sulphate. Evaporation of the ether gave a semi-solid (1 g) which crystallised on addition of ethanol. Recrystalisation from ethanol gave 4-(6'-methoxy-2'-naphthyl)-butan-2-one (520 mg) m.p. 80° C.

EXAMPLE 20

4-(6-Methoxy-2-naphthyl)-3-buten-2-one

6-Methoxy-2-naphthaldehyde (30 g) was stirred in acetone (500 ml) with sodium hydroxide (10 mls of 10% aqueous solution) for 3 hours. The solution was acidified and extracted with ether. The ether solution was dried (MgSO$_4$) and evaporated under reduced pressure to yield a solid (30 g). This impure material was purified on a silica gel column using benzene as eluant to give 4-(6-methoxy-2-naphthyl)-3-buten-2-one (15 g). mp. 120° C.

EXAMPLE 21

4-(6-Methoxy-2-naphthyl)butan-2-one 4-(6-Methoxy-2-naphthyl)-3-butene-2-one (32 g) in ethyl acetate (500 ml) was shaken at room temperature over 10% Pd/C (3 g) under atmospheric pressure hydrogen until no further uptake of hydrogen occurred to yield 4-(6-methoxy-2-naphthyl)butan-2-one (22.5 g), mp. 78.5° C.

EXAMPLE 22

4-(6-Methoxy-2-naphthyl)-butan-2-one

A mixture of 6-methoxy-2-bromonomethylnaphthylene (0.1 mole), acetylacetone (0.1 mole) and potassium carbonate (0.1 mole) in ethanol (125 ml) was refluxed for 16 hours. The ethanol was evaporated off under reduced pressure and the residue was shaken with a water/ether mixture (400 mls, 1:1). The ether layer was dried (MgSO$_4$) and evaporated in vacuo to leave a clear oil which after purification yielded solid 4-(6-methoxy-2-naphthyl)-butan-2-one.

EXAMPLE 23

Pharmacalogical data

Using a conventional Allen-Doisy Test, the Oestrogenic activity of certain compounds of the invention was ascertained. The results are shown in Table 1. The anti-inflammatory activity of certain compounds of the invention was ascertained by using a standard Rat Paw Carrageenin Test. These results are also shown in Table 1.

These results show that compounds of this invention have a good level of activity at a dosage where excessive oestrogensity is not to be expected. Further, it is believed that an absence of brancing at the α-carbon atom reduces greatly any oestrogenicity which might be present while not effecting the anti-inflammatory activity of the compounds to any great extent.

It has further been observed that compounds of the formula:

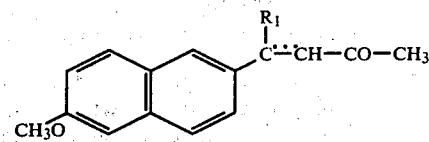

wherein R$_1$ is H or CH$_3$ and the dotted line represents a double bond optionally present, do not excessively irritate the rat stomach at a dose of 300 mg/kg/day orally after 3 days while at the end of 1½ days oral treatment with the compound of formula (I), very severe gastric irritation was noted at the same dose level.

TABLE 1

| COMPOUND | OESTROGENICITY ALLAN-DOISY TEST | ANTI-IN-FLAMMATORY RAT CARRAGEENAN |
|---|---|---|
| 3-(6'-methoxy-2'-naphthyl)-butan-2-one | 50 mg/kg sub.cut., Inactive (mouse) 600 mg/kg orally, Inactive (rat) | 100 mg/kg orally, Active Active |
| 3-Hydroxy-3-methyl-4-(6'-methoxy-2'-naphthyl)-pentan-2-one | 100 mg/kg sub.cut., Active (mouse) | 50 and 100 mg/kg orally, Active |
| 3-Hydroxy-3-methyl-4-(6'-methoxy-2'-naphthyl)-hexan-2-one | 50 mg/kg sub.cut., Active (mouse) | 100 mg/kg orally, Inactive |
| 4-(6'-methoxy-2'-naphthyl)-pent-3-en-2-one | 100 mg/kg sub.cut., Inactive (mouse) | 100 mg/kg orally, Active Active |
| 4-(6'-methoxy-2'-naphthyl)-pentan-2-one | 300 mg/kg orally, Active (rat) | 300 mg/kg orally, Active Active |
| 4-(6'-methoxy-2'-naphthyl)-pentan-2-one | 200 mg/kg orally, Inactive (rat) | 50 mg/kg orally, Slightly Active 100 mg/kg orally, Active 1 hr. after dosing* |
| 4-(6'-methoxy-2'-naphthyl)-3-butene-2-one | 300 mg/kg, orally, Inactive (rat) | 300 mg/kg orally, Active. |

*ASPIRIN (300 mg/kg) GIVES EQUIVALENT ACTIVITY 2 HRS. AFTER DOSING

EXAMPLE 24

Crystalline 4-(6'-methoxy-2'-napthyl)butan-2-one

Non-crystalline 4-(6'-methoxy-2'-naphthyl)butan-2-one (32 g; prepared as in Example 21) was dissolved with boiling in ethanol (134 ml IMS) and cooled to 5° C. to give a first crop of 11.26 g. The mother liquor was stripped to dryness under reduced pressure at 40° C. to yield 20.7 g of material. This was dissolved in ethanol (40 ml) with boiling and then cooled to 0° C. The product was filtered off and washed with cold ethanol (25 ml) to give a second crop of 6.1 g. The two crops were combined and dissolved with boiling in ethanol (73 ml). The solution was cooled to 0° C. and the product filtered off, washed with cold ethanol (26 ml) and dried to give a crystalline product (12.4 g). This was dissolved in boiling ethanol (45 ml) and allowed to cool to 20° C. The resulting crystals were filtered off and dried to give 11.8 g of the desired crystalline 4-(6'-methoxy-2'-naphthyl)butan-2-one m.p. 79°–80° C.

EXAMPLE 25

Test Data for 4-(6'-Methoxy-2'-naphthyl)butan-2-one 4-(6'-methoxy-2'-naphthyl)butan-2-one has a good spectrum of anti-inflammatory activity while being free of hormone like activity and showing a good therapeutic ratio based on gastro intestinal irritancy. The compound also has other properties desirable in an anti-inflammatory agent for the treatment of rheumatic diseases, for example anti-pyretic and analgesic activity. The following summary of test data obtained for 4-(6'-methoxy-2'-naphthyl)butan-2-one supports the preceding statements:

a. Carrageenin Induced Oedema in Rats.

A significant reduction in induced oedema volume was found with doses of 5, 10, 35 and 70 mg/kg p.o. An $ED_{25}$ value of about 7-10 mg/kg p.o. is indicated. Activity is maintained in adrenalectomised rats.

b. UV Induced Erythrema in Guinea Pigs.

A $ED_{50}$ value of about 9-15 mg/kg p.o. was found on this test.

c. Cotton Pellet Induced Granuloma in Rats.

Consistent activity (reducing induced granuloma by more than 30%) has been observed at 50 mg/kg p.o. dosed from day 0 to 5 days. The activity in this test is not accompanied by marked changes in body weight or in the weight of the spleen, thymus, kidney, liver or adrenal glands.

d. Adjurant Arthritis in Rats.

Adjuvant arthritis is reduced in rats by the daily administration of doses of 60 mg/kg p.o.

e. Macrophage Plasmongen Activator Release test.

On the test system of J. D. Vassalli et. al., Cell, 8, 271-281 (1976), the compound at 10 mg/ml caused 90% inhibition of the release of plasmogen activator from cultured mouse peritoneal macrophages. A level of 1 mg/ml of the compound caused slight inhibition.

f. Phenyl-p-quinone Induced Writhing in Mice.

An $ED_{50}$ value for analgesic activity of about 110 mg/kg p.o. was obtained (acetylsalicylic acid has an $ED_{50}$ of about 60 mg/kg p.o.)

g. Anti-pyretic Effect in Rabbits.

The compound reduced pyresis induced by intraveous injection of Shigella endotoxin at doses down to 100 mg/kg p.o.

h. Interactions with the Adrenal/Pitutary Axis.

Five days dosed at 140 mg/kg p.o./day does not interfere with release of corticosteroids from the adrenal gland as a response to ACTH administration or to ether stress.

i. Oestrogenic Test in Rats.

Doses of 200 mg/kg p.o. and 600 mg/kg p.o. given for 4 days to ovariectomised rats did not result in any increase in uterine weight.

j. Anabolic/Adrogenic Activity in Rats.

Doses of 200 mg/kg p.o. given to castrated young male rats for 4 days did not result in any increase in the weight of seminal vesicles, prostate gland or levator ani muscles. The same dose did not interfere with the androgenic/anabolic activity of concominantly administered testosterone (1 mg/kg s.c.).

k. Gestagenic Activity in Rabbits.

In the Clauberg test doses of 200 mg/kg p.o. for 4 days did not result in uterine hypertrophy or progestational changes in the endometrium.

l. Gastric Damage in Pyloric Ligated Rats.

Doses of up to 200 mg/kg applied intra-duadenally in the pyloric ligated rat have not been found to have a systemically mediated effect on the volume of gastric secretion nor did overt gastric damage result.

m. Ulcerogenic Activity in Rats.

Doses of 250 mg/kg p.o. or 500 mg/kg p.o. administered to rats starved for 18 hours did not give rise to gastric erosions or ulceration when the time between dosing and examination was 1 or 4 hours. Longer contact times did lead in some cases to some degree of erosions. Long term toxicity tests have shown doses of 180 mg/kg p.o. for 28 days to be well tolerated with regard to the gastro intestinal tract.

What is claimed is:

1. 4-(6'-methoxy-2'-naphthyl)butan-2-one having a melting point of not less than 78.5° C.

2. 4-(6'-Methoxy-2'-naphthyl)butan-2-one in solid form.

3. Crystalline 4-(6'Methoxy-2'naphthyl)butan-2-one having a melting point of approximately 80° C.

4. 4-(6'-Methoxy-2'-naphthyl)butan-2-one.

* * * * *

UNITED STATES PATENT AND TRADEMARK OFFICE

CERTIFICATE EXTENDING PATENT TERM
UNDER 35 U.S.C. § 156

PATENT NO.:      4,420,639

DATED:           December 13, 1983

INVENTORS:       Anthony W. Lake et al.

PATENT OWNER:    Beecham Group p.l.c.

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

2 YEARS with all rights pertaining thereto as provided by 35 U.S.C. § 156(b).

I have caused the seal of the Patent and Trademark Office to be affixed this 20th day of May 1993.

Michael K. Kirk
Acting Commissioner of Patents and Trademarks

UNITED STATES PATENT AND TRADEMARK OFFICE
CERTIFICATE OF CORRECTION

PATENT NO. : 4,420,639

DATED : December 13, 1983

INVENTOR(S) : ANTHONY W. LAKE, ET AL.

It is certified that error appears in the above-identified patent and that said Letters Patent is hereby corrected as shown below:

ON THE TITLE PAGE AT [60] RELATED U.S. APPLICATION DATA:

In the fourth line, "Pat. No. 4,061,799" should read --Pat. No. 4,061,779--.

In the sixth line, "Ser. No. 501,733" should read --Ser. No. 501,773.

IN THE SPECIFICATION:

At Col. 1, lines 8-9, "U.S. Pat. No. 4,061,799" should read --U.S. Pat. No. 4,061,779--.

At Col. 1, line 12, "Ser. No. 501,733" should read --Ser. No. 501,773--.

Signed and Sealed this

Sixth Day of February, 2001

Attest:

Q. TODD DICKINSON

*Attesting Officer*      *Director of Patents and Trademarks*

(12) REEXAMINATION CERTIFICATE (4418th)
United States Patent
Lake et al.

(10) Number: US 4,420,639 C1
(45) Certificate Issued: Aug. 21, 2001

(54) AROMATIC COMPOUNDS

(75) Inventors: Anthony W. Lake, Guildford Surrey; Carl J. Rose, London, both of (GB)

(73) Assignee: Beecham Group Limited (GB)

Reexamination Request:
No. 90/005,687, Mar. 29, 2000

Reexamination Certificate for:
Patent No.: 4,420,639
Issued: Dec. 13, 1983
Appl. No.: 06/320,190
Filed: Nov. 12, 1981

Certificate of Correction issued Feb. 6, 2001.

Related U.S. Application Data

(63) Continuation of application No. 05/955,197, filed on Oct. 27, 1978, now abandoned, which is a continuation of application No. 05/795,119, filed on May 9, 1977, which is a division of application No. 05/748,676, filed on Dec. 8, 1976, now Pat. No. 4,061,779, which is a continuation-in-part of application No. 05/563,159, filed on Mar. 28, 1975, now abandoned, which is a division of application No. 05/501,773, filed on Aug. 29, 1974, now abandoned.

(30) Foreign Application Priority Data

Sep. 11, 1973 (GB) .................................................. 42550/73

(51) Int. Cl.$^7$ ................................................. C07C 49/215
(52) U.S. Cl. .............................................................. 568/328
(58) Field of Search ............................................... 568/328

(56) References Cited

U.S. PATENT DOCUMENTS 3,641,161    2/1972   Fried .
3,969,382  * 7/1976   Zosel ..................................... 260/409

FOREIGN PATENT DOCUMENTS

| 819794  | 3/1975  | (BE) . |
| 2051012 | 10/1970 | (DE) . |
| 2242972 | 9/1974  | (FR) . |
| 2442305 | 9/1974  | (DE) . |
| 1291386 | 1/1970  | (GB) . |

OTHER PUBLICATIONS

Morrison & Boyd, Organic Chemistry, 1996, p. 567.

Schwenk and Bloch, "A New Modification of Willgerodt's Reaction," *J. Am. Chem. Soc.* vol. 70, 1970, pp. 3051–3052.

McKillop, *J. Am. Chem. Soc.*, vol. 95, May 16, 1973, p. 3340.

Harrison et al., "Non Steroidal Anti–inflammatory Agents, I. 6–Substituted 2–Naphthyl Acetic Acids," *J. Med. Chem.*, vol. 13, 1970, p. 203.

Fried et al., "Structure Activity Relationship Among 6–Substituted–2–Naphthyl Acetic Acids," *Second J. Rheum.*, Supp 2, 1973, pp. 7–11.

Williams, *Detoxication Mechanisms*, 2$^{nd}$ Ed, 1959 pp. 3336–3338.

* cited by examiner

*Primary Examiner*—Sreeni Padmanabhan

(57) ABSTRACT

4-(6'-Methoxy-2'-naphthyl) butan-2-one is described as having anti-inflammatory activity and an improved therapeutic ratio.

US 4,420,639 C1

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 2 and 4 is confirmed.

Claims 1 and 3 are cancelled.

New claims 5–7 are added and determined to be patentable.

*5. 4-(6'-methoxy-2'-naphthyl) butan-2-one having a melting point of 78.5° C.*

*6. 4-(6'-methoxy-2'-naphthyl) butan-2-one in solid form having a melting point of 78.5° C.*

*7. Solid 4-(6'-methoxy-2'-naphthyl) butan-2-one having anti-inflammatory properties.*

\* \* \* \* \*